United States Patent
Brett (10) Patent No.: US 6,916,328 B2
(45) Date of Patent: Jul. 12, 2005

(54) PERCUTANEOUS CELLULITE REMOVAL SYSTEM

(75) Inventor: Darrell C. Brett, Portland, OR (US)

(73) Assignee: Expanding Concepts, L.L.C, Portland, OR (US)

( * ) Notice: Subject to any disclaimer, the term of this patent is extended or adjusted under 35 U.S.C. 154(b) by 262 days.

(21) Appl. No.: 10/202,415

(22) Filed: Jul. 22, 2002

(65) Prior Publication Data

US 2003/0158566 A1 Aug. 21, 2003

Related U.S. Application Data

(60) Provisional application No. 60/356,891, filed on Feb. 13, 2002, and provisional application No. 60/332,355, filed on Nov. 15, 2001.

(51) Int. Cl.$^7$ ............................................. A61B 17/32
(52) U.S. Cl. .................. 606/167; 606/169; 606/39; 606/180; 606/2; 606/171; 606/177
(58) Field of Search ........................... 604/272, 19, 22, 604/35, 507, 571, 131, 151, 152, 158–163, 164.01, 164.06, 218, 224, 228, 264; 600/201; 606/1, 2, 39–50, 159, 167–177, 180, 184, 185, 107, 187

(56) References Cited

U.S. PATENT DOCUMENTS

| | | | |
|---|---|---|---|
| 3,526,219 A | | 9/1970 | Balamuth |
| 4,191,191 A | | 3/1980 | Auburn |
| 4,530,359 A | * | 7/1985 | Helfgott et al. ............. 606/171 |
| 4,536,180 A | | 8/1985 | Johnson |
| 4,735,605 A | | 4/1988 | Swartz |
| 4,886,491 A | | 12/1989 | Parisi et al. |
| 5,106,376 A | * | 4/1992 | Mononen et al. ...... 604/164.11 |
| 5,360,416 A | * | 11/1994 | Ausherman et al. ........ 604/272 |
| 5,419,761 A | | 5/1995 | Narayanan et al. |
| 5,470,308 A | * | 11/1995 | Edwards et al. ............... 604/22 |
| 5,499,991 A | | 3/1996 | Garman et al. |
| 5,569,291 A | | 10/1996 | Privitera et al. |
| 5,584,847 A | | 12/1996 | Duluco et al. |
| 5,690,664 A | | 11/1997 | Sauer et al. |
| 5,778,894 A | | 7/1998 | Dorogi et al. |

(Continued)

OTHER PUBLICATIONS

U.S. Appl. No. 60/348,301, filed Nov. 2001, Hinchliffe et al.*

(Continued)

*Primary Examiner*—Glenn K. Dawson
(74) *Attorney, Agent, or Firm*—Karen Dana Oster (57) ABSTRACT

A percutaneous cellulite removal needle of the present invention can be used to make the appearance of cellulite less obvious by cutting the fibrous bridges that connect the skin to muscle/fascia or fibrous septae in the subcutaneous fat in a minimally invasive manner. The percutaneous cellulite removal needle of the present invention preferably includes a body having an internal chamber that ends at a laterally disposed aperture. A cutting mechanism is substantially positioned within the internal chamber in a retracted position and at least partially protrudes through the laterally disposed aperture in a cutting position. A situating mechanism transitions the cutting mechanism between the retracted position and the cutting position. The present invention also includes a method in which the percutaneous cellulite removal needle is inserted through the skin with the cutting mechanism in the retracted position. The cutting mechanism is then extruded so that the cutting mechanism is in the cutting position. Next the cutting mechanism is actuated, for example by rotating, to cut at least one the fibrous bridge or septae. These steps may be repeated to cut other fibrous bridges or septae reachable by the cutting mechanism. The cutting mechanism is then retracted and the percutaneous cellulite removal needle is removed.

36 Claims, 7 Drawing Sheets

U.S. PATENT DOCUMENTS

| | | | |
|---|---|---|---|
| 5,797,944 A | | 8/1998 | Nobles et al. |
| 5,800,389 A | * | 9/1998 | Burney et al. .......... 604/164.01 |
| 5,810,863 A | | 9/1998 | Wolf et al. |
| 5,884,631 A | * | 3/1999 | Silberg ....................... 128/898 |
| 5,911,700 A | | 6/1999 | Mozsary et al. |
| 5,980,493 A | | 11/1999 | Smith et al. |
| 6,078,842 A | | 6/2000 | Gross et al. |
| 6,120,517 A | * | 9/2000 | Daum et al. ................. 606/167 |
| 6,142,955 A | | 11/2000 | Farascioni et al. |
| 6,152,894 A | | 11/2000 | Kubler |
| 6,200,313 B1 | * | 3/2001 | Abe et al. ...................... 606/34 |
| 6,231,514 B1 | | 5/2001 | Lowe et al. |
| 6,503,263 B2 | | 1/2003 | Adams |
| 6,520,927 B1 | * | 2/2003 | Unsworth .................... 604/19 |
| 2002/0143302 A1 | * | 10/2002 | Hinchliffe et al. .......... 604/272 |

OTHER PUBLICATIONS

Clara Liebman, M.D. and Joseph Cohen, M.D. "Surgical Treatment of Cellulite and its Results, American Journal of Cosmetic Surgery," 299–303, vol. 16, No. 4.

Lisette Hilton, "Cellulite Problem Eliminated By Removing 'Fibrous Bridges,'" Dermatology Times, Mar. 2000. (Printed Apr. 2, 2001 from the internet.).

"Cellulite," MedicineNet.com. At least as early as Jul. 10, 2001.

"Cellulite Treatment: Surgical," eBody.com, Jul. 11, 2001.

"Procedures Cellulite Treatment," Ienhance. (Printed from www.ienhance.com.) At least as early as Jul. 10, 2001.

"Innovation: Ultracision Harmonic Scalpel: Advances in Laparoscopic Surgical Procedures," Johnson & Johnson. Printed from www.jnj.com on Jul. 10, 2001.

* cited by examiner

PERCUTANEOUS CELLULITE REMOVAL SYSTEM

The present application is based on, and claims priority from, U.S. Provisional Application Ser. No. 60/332,355, filed Nov. 15, 2001 and U.S. Provisional Application Ser. No. 60/356,891, filed Feb. 13, 2002, both of which are hereby incorporated herein by reference.

BACKGROUND OF INVENTION

The present invention relates to an apparatus and method for making the appearance of cellulite less obvious by cutting the fibrous bridges that connect the skin to muscle and/or fascia (hereinafter referred to as "muscle," "fascia," or "muscle/fascia") or by cutting the fibrous septae in subcutaneous fat in a minimally invasive manner, and specifically to a percutaneous cellulite removal needle with at least one lateral opening in its peripheral surface through which a surgical instrument and/or a cutting mechanism retracts or protrudes and methods for using the percutaneous cellulite removal needle.

Cellulite is a popular term used to describe the dimpled or "lumpy skin" appearance of the skin that some people have on their hips, thighs, and buttocks. Cellulite often occurs in women who are not particularly overweight or a good candidate for liposuction. It is caused by a "buttoning" or "mattress effect" of the skin 24 with tethering of the dermis 22 to the underlying muscle or fascial layers 26 by fibrous bands 28 or by fibrous septae in the subcutaneous fat.

Dietary supplements, topical creams, massage treatments, and other methods have been suggested for treatment of cellulite. There are few scientific studies, however, that demonstrate the efficacy of any of these methods. Nor is liposuction—a surgical technique for extracting fat by vacuuming it from under the skin—always an effective treatment for cellulite. This is because the dimpled appearance is the result of deposits of subcutaneous fat in combination with the fibrous bridges that attach the skin to underlying muscle. When the fibrous bridges tighten, the skin is pulled tight over the deposits of subcutaneous fat creating a dimpled appearance. Removal of the subcutaneous fat by liposuction does not alter the dimpled appearance of the skin and, in fact, may worsen the appearance of the skin. In order to smooth the skin, it is necessary to break the fibrous bridges.

A method for the treatment of cellulite by breaking fibrous bridges is disclosed in *Surgical Treatment of Cellulite and its Results*, by Clara Lieberman, M.D. and Joseph Cohen, M.D., American Journal of Cosmetic Surgery, Vol. 16, No. 4, 1999, 299–303. The Lieberman-Cohen method is a surgical treatment using liposuction and release of the fibrous tissue bridges with blunt thin cannulas. Specifically, the cannulas break the fibrous bridges that originate from the herniation of subcutaneous fat. While this method represents a significant advance in the treatment of cellulite, a disadvantage of this method is that it uses an instrument that was not designed for the purpose of cutting fibrous bridges or septae. The use of a liposuction cannula is invasive, awkward, imprecise, and physically difficult.

Because treatment of cellulite by breaking fibrous bridges or septae is a recent development, prior art surgical devices were not developed with this purpose in mind. Prior art cutting devices generally contemplate cutting tissue other than fibrous bridges using a cutting mechanism located at the distal tip of the device. Several representative prior art devices are described below. Each of the devices described would need to be used in the same manner that the liposuction cannula is employed in the Lieberman-Cohen method and suffers from the same and additional disadvantages.

U.S. Pat. No. 3,526,219 to Balamuth (the "Balamuth reference") is directed to a method and apparatus for ultrasonically microchopping tissue and removing the tissue fragments from a body. The Balamuth device has a fine edge that is vibrated in the ultrasonic frequency range and accelerated above 50,000 g to produce a tissue breakdown fundamentally different from tissue slicing. A fluid stream controls temperature while a built-in suction machine removes tissue and fluid. Because the Balamuth fine edge is located at the distal tip, the device is adapted only for removal of tissue directly ahead of the distal tip.

U.S. Pat. No. 5,690,664 to Sauer et al. is directed to a laparoscopic trocar that has a cutting blade positioned inside the distal tip of the trocar for penetrating the peritoneum. The Sauer trocar is pistol-shaped and an operator deploys the distally located cutting blade by pulling a trigger. Movement of the cutting blade between the non-deployed and deployed positions facilitates tissue penetration by cutting the tissue directly ahead of the distal tip of the trocar.

An example of a surgical cutting instrument for removing sections of bodily tissue taking a slightly different approach from the devices discussed above is U.S. Pat. No. 6,152,894 to Kubler (the "Kubler reference"). The Kubler instrument is a pointed linear shank percutaneously insertable through a trocar. Once inserted, an external actuator pulls a cord inside the device that deforms the distal end of the shank into a curved sickle shape. Cutting blades are arranged along the inside curve of the curved sickle and a spherical piece of tissue located at the end of the shank may be excised by rotating the shaft of the Kubler device. Although the Kubler approach is somewhat different, the tissue cut is still directly ahead of the distal tip of the device.

U.S. Pat. No. 5,419,761 to Narayanan et al. (the "Narayanan reference") is directed to a cannula for an ultrasonic liposuction method. The Narayanan cannula transmits an ultrasonic wave through the cannula producing cavitation at the distal tip. Adipose tissue is liquefied in front of the distal tip and aspirated through a bore in the cannula. A disadvantage of the Narayanan cannula is that the intensity of the ultrasonic wave would likely need to be increased substantially to sever fibrous tissue and this increase would likely result in unwanted ancillary damage to nearby tissue. In addition, the tissue acted upon is still directly ahead of the distal tip of the device.

U.S. Pat. No. 5,569,291 to Privitera et al. (the "Privitera reference") is directed to a surgical penetration instrument for dissection having a tube through which an endoscope can be inserted. The endoscope locks into place so that movement relative to the tube is prevented. A conical transparent tip on the tube allows the endoscope to visualize the insertion path and treatment site. The conical tip has two blades positioned 180 degrees apart that extend longitudinally from the tip to the base of the conical tip. The blades are for facilitating insertion and cutting target tissues. The Privitera device views and cuts tissue only directly ahead of the distal tip.

U.S. Pat. No. 5,797,944 to Nobles et al. (the "Nobles reference") is directed to a laparoscopic trocar allowing a view. The Nobles trocar has blades positioned on a pointed head for percutaneous insertion. A slanted window on the pointed head and a hollow shaft allow visualization by an optional endoscope. The Nobles reference provides a view only directly ahead of the distal tip of the device.

BRIEF SUMMARY OF THE INVENTION

The present invention relates to an apparatus and method for making the appearance of cellulite less obvious by cutting the fibrous bridges that connect the skin to muscle or the fibrous septae in subcutaneous fat in a minimally invasive manner, and specifically to a percutaneous cellulite removal needle with at least one lateral opening in its peripheral surface through which a surgical instrument and/ or a cutting mechanism retracts or protrudes and methods for using the percutaneous cellulite removal needle.

A percutaneous cellulite removal needle of the present invention includes a body having an internal chamber that ends at a laterally disposed aperture defined in the outer peripheral surface of the body. A cutting mechanism is substantially positioned within the internal chamber in a retracted position and at least partially protrudes through the laterally disposed aperture in a cutting position. A situating mechanism transitions the cutting mechanism between the retracted position and the cutting position. Additional chambers for additional surgical instruments may be incorporated in the invention.

The present invention also includes a method for cutting fibrous bridges that connect skin to muscle or the fibrous septae in subcutaneous fat in a minimally invasive manner. In this method the percutaneous cellulite removal needle is inserted through the skin with the cutting mechanism in the retracted position. The cutting mechanism is then extruded so that the cutting mechanism is in the cutting position. Next the cutting mechanism is actuated, for example by rotating, to cut at least one the fibrous bridge. These steps may be repeated to cut other fibrous bridges reachable by the cutting mechanism. The cutting mechanism is then retracted and the percutaneous cellulite removal needle is removed.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
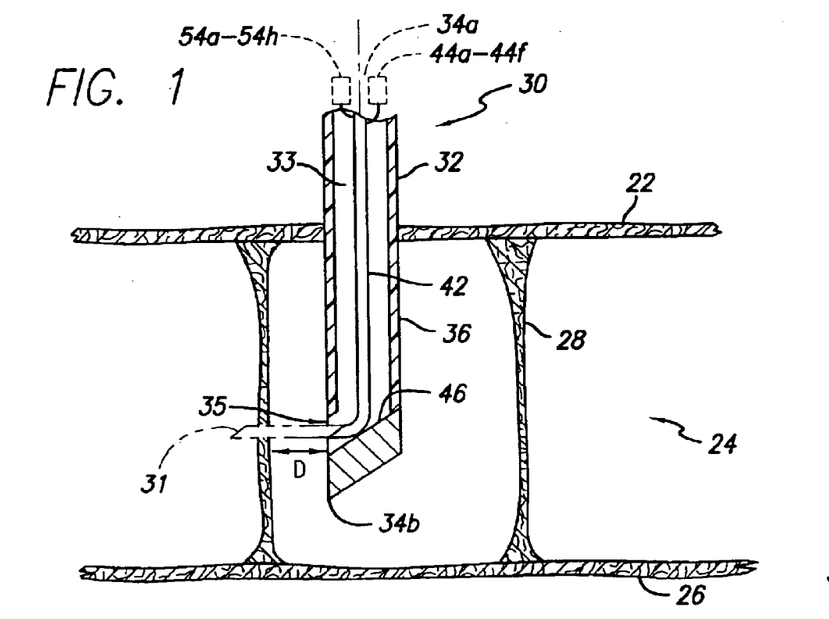
FIG. 1 is a side cross-sectional view of a generic preferred embodiment of the percutaneous cellulite removal needle of the present invention showing a flexible, retractable cutting mechanism in an extended, cutting position.

As shown in FIGS. 1–4, the present invention is directed to a percutaneous cellulite removal needle 30 (exemplary preferred embodiments are labeled as 30i a(FIG. 2), 30b (FIG. 3), and 30c (FIG. 4)) that includes a surgical instrument (shown individually as 29a–29k, but discussed as a group as 29) such as a flexible blade or other cutting mechanism 31 for cutting the fibrous bridges 28 or the fibrous septae in subcutaneous fat that connect the dermis 22 to muscle/fascia 26 in a minimally invasive manner. Throughout the remainder of this disclosure, the fibrous bridges 28 will be discussed, but the same principles can be applied to fibrous septae in subcutaneous fat. FIG. 1 shows a generic or basic percutaneous cellulite removal needle 30 of the present invention that will be used to discuss some of the features of the various embodiments.

The Body. The main housing or body 32 of the percutaneous cellulite removal needle 30 consists of a slender, elongated, hollow tube with an internal chamber 33 that houses the cutting mechanism 31. The body 32 may be rigid or flexible. In shown preferred embodiments, the body 32 has a proximal end 34a which remains outside the human body and a closed distal end 34b suitable for penetrating tissue and insertion within the human body. The internal chamber 33 preferably ends in a lateral aperture 35 formed in the outer peripheral surface 36 of the body 32 near the distal end 34b. The body 32 may have a cross section of any shape and, for exemplary purposes only, is being shown as a circular cross section. Similarly, the internal chamber 33 may have a cross section of any shape and, for exemplary purposes only, is being shown as circular. The outer peripheral surface 36 is preferably smooth to aid in insertion.

For purposes of describing the present invention, the term "needle" means a slender, elongated, hollow instrument with a lateral opening in its peripheral surface. It should be understood that the term needle, as used herein, includes a needle, a trocar, a trocar obturator, a trocar cannula, a tube, a cylinder or any other slender, elongated, hollow instrument or device suitable for use in the surgical procedure of the present invention. The term "needle" further refers to any slender, hollow, sharp-pointed instrument for puncturing tissue and introducing material into a human body. A trocar (or trocar obturator or obturator) commonly refers to an elongated, cylindrical shaft or rod with a sharp tip capable of penetrating tissue and is ordinarily used with a cannula (or trocar cannula). A trocar cannula is an elongated hollow tube that functions as a sleeve for the trocar obturator. In use, the trocar obturator is slid into the trocar cannula and the assembly is advanced into tissue. After the assembly has penetrated the human body wall, the trocar obturator is withdrawn leaving the trocar cannula. The trocar cannula may be used to withdraw fluids from various body cavities, or used as a passage way for the insertion and withdrawal of surgical instruments in procedures such as endoscopic surgery. The term trocar also refers to the assembly of the trocar obturator and trocar cannula. In addition, the terms trocar or cannula may also refer to specialized surgical instruments adapted from the traditional trocar obturator/cannula assembly, such as a cannula that serves as a passageway for an aspirator in liposuction procedures. The percutaneous cellulite removal needle 30 may be any of these needles.

Figure 5:
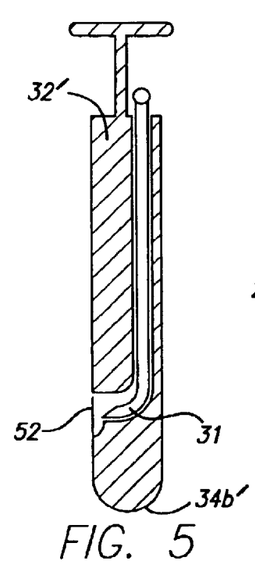
FIG. 5 is a side cross-sectional view of an exemplary embodiment of the percutaneous cellulite removal needle of the present invention showing, a substantially solid body embodiment, the internal chamber formed as a guide shaft, and the lateral aperture having a cover.

In one preferred embodiment, a sharp blade-like edge distal end 34b facilitates penetration of tissue. The blade-like edge distal end 34b may be an integral or separate component removably attached to percutaneous cellulite removal needle 30. In addition, the blade-like edge distal end 34b may consist of two or more blades. In an alternative preferred embodiment, the distal end 34b is rounded and blunt, as shown in FIG. 5. This blunt embodiment is advantageous when percutaneous cellulite removal needle 30 is inserted into an incision made by another instrument and/or protection of tissue directly ahead of the percutaneous cellulite removal needle 30 is desired. Other shapes for distal end 34b are contemplated, such as conical. The choice of shape for distal end 34b depends on the surgical site where the method of the present invention will be performed and the preferences of the surgeon.

The Lateral Aperture. The lateral aperture 35 is preferably formed in the outer peripheral surface 36 near the distal end 34b of the percutaneous cellulite removal needle 30. This location provides the advantage of minimizing the depth that the percutaneous cellulite removal needle 30 should be inserted. But the lateral aperture 35 need not be formed near the distal end 34b. In alternative exemplary embodiments, the lateral aperture 35 may be formed at any point between the proximal and distal ends 34a, 34b.

In addition, in alternative preferred embodiments the percutaneous cellulite removal needle 30 may include two or more lateral apertures 35 (e.g. two lateral apertures 35 formed on the same side of the percutaneous cellulite removal needle 30 (FIG. 6) or lateral apertures 35 formed on the opposite sides of the percutaneous cellulite removal needle 30 (FIG. 7)).

The lateral aperture 35 may be round, oval, rectangular, or any other suitable shape.

To prevent tissue and fluids from entering the internal chamber 33, the lateral aperture 35 may have a cover 52 (FIGS. 4 and 5) associated with it that may be closed (FIG. 5) to facilitate insertion and removal of the surgical percutaneous cellulite removal needle 30, and opened (FIG. 4) when the surgical percutaneous cellulite removal needle 20 is in its cutting position. The cover 52 may hold and/or support the cutting mechanism 31 at a desired angle (shown as a right angle, but any angle could be accomplished). The cover 52 may be self-sealing. For example, in one alternative embodiment (not shown) it could be a self-sealing membrane. It should be noted that the cover 52 is an optional feature of the present invention.

The Cutting Means. The cutting mechanism 31 of the present invention is shown as a thin flexible blade for cutting fibrous bridges 28. The shown flexible blade 31 may extend through the lateral aperture 35 approximately 0.5 to 3 cm. The width of flexible blade 31 may be 1 to 5 mm. These dimensions, however, are exemplary and other dimensions are contemplated. In addition, it is contemplated that the cutting mechanism 31 may be any of a variety of apparatus known in the art for cutting tissue, such as a cautery (shown as 29b in FIG. 6), a harmonic scalpel (shown as 29c in FIG. 6), an ultrasonic cutting instrument (shown as 29d in FIG. 6), a rotary cutter (shown as 29e in FIG. 6), a laser cutter (shown as 29f in FIG. 6), an oscillating saw (shown as 29g in FIG. 6), or any other suitable cutting apparatus. Devices known in the art for cutting tissue are collectively referred to herein as cutting mechanisms 31.

The cutting mechanism 31 preferably moves between two positions: a retracted position in which the cutting mechanism 31 is within the internal chamber 33 and a cutting position (in phantom) in which the cutting mechanism 31 extends through the lateral aperture 35 to the side of the percutaneous cellulite removal needle 30. In the retracted position, the cutting mechanism 31 is substantially contained within the internal chamber 33 and may rest on or near a guide surface 46 formed by the closed distal end 34b. In the cutting position, the cutting mechanism 31 may be substantially perpendicular to the longitudinal axis of the percutaneous cellulite removal needle 30. (The longitudinal axis is an imaginary line running through the center of percutaneous cellulite removal needle 30 from the proximal end 34a to the distal end 34b.) The guide surface 46 serves to guide the cutting mechanism 31 from its retracted position to its cutting position, and may be, for example, sloped, curved, or flat.

Figure 8:
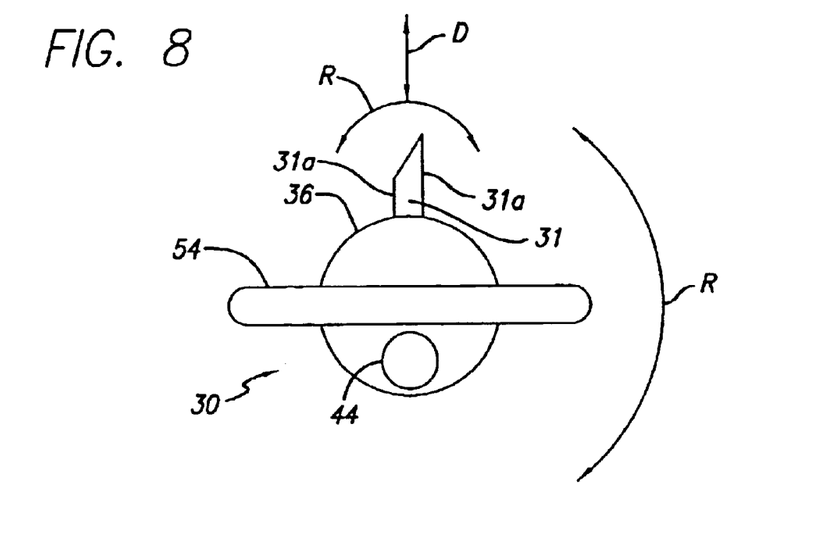
FIG. 8 is a top view of an exemplary embodiment of the percutaneous cellulite removal needle of the present invention showing directions of movement to sever fibrous bridges.

FIG. 8 shows a top view of an exemplary percutaneous cellulite removal needle 30 in the cutting position with the cutting mechanism 31 extending out of the internal chamber 33. In the shown embodiment, the cutting mechanism severs fibrous bridges 28 as it is moved in the direction of action arrow R. Alternatively, or in combination, the cutting mechanism 31 may have a sharp tip for cutting. In this embodiment, the cutting mechanism 31 severs fibrous bridges 28 as it is moved in the direction of action arrow D.

The Situating Means. A situating mechanism 44 (the reference numeral 44 (as shown in FIG. 8) is a general reference to any type of situating mechanism including, but not limited to exemplary situating mechanisms 44a–44f (FIG. 1)) controls the transition of the cutting mechanism 31 between the retracted position in which the cutting mechanism 31 is within the internal chamber 33 and the cutting position in which the cutting mechanism 31 extends through the lateral aperture 35 to the side of the percutaneous cellulite removal needle 30. Exemplary situating mechanisms 44 may include an extrusion mechanism 44a (FIG. 2) such as a button or lever that maybe slid between two positions, a handle 44b (FIG. 3) that may be pulled up or pushed down, a dial 44c (FIG. 4) that may be rotated between two positions, a ratchet, or any device capable of having two positions. FIG. 1 shows exemplary situating mechanisms (e.g. an extrusion mechanism, a button, a lever, a handle, a dial, or a ratchet) represented in phantom as 44a–44f. These situating mechanisms are meant to be exemplary and are not meant to limit the scope of the invention.

Figure 2:
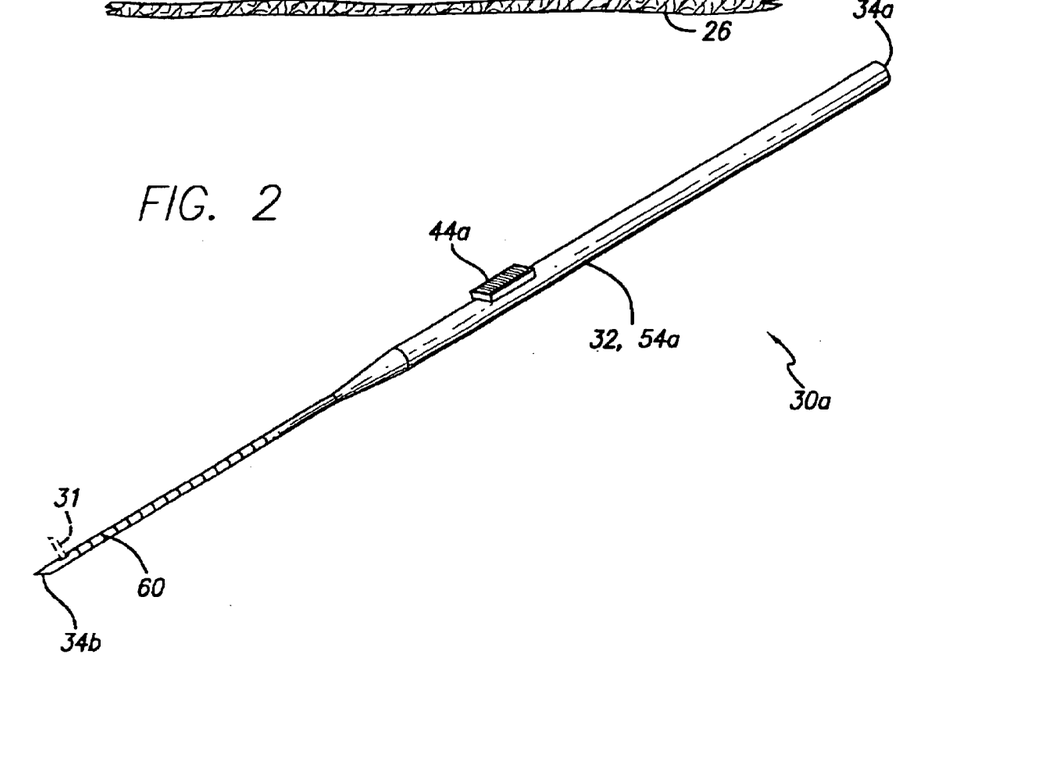
FIG. 2 is a perspective view of a first exemplary embodiment of the percutaneous cellulite removal needle of the present invention.

The Connecting Means. In a preferred embodiment, a connecting member 42 is contained within internal chamber 33. One end of the connecting member 42 is functionally connected to the cutting mechanism 31. The other end of the connecting member 42 is functionally connected to the situating mechanism 44. The present invention, however, contemplates alternatives to connecting member 42. In one preferred embodiment, the cutting mechanism 31 extends the length of internal chamber 33 and attaches directly to situating mechanism 44, eliminating the need for connecting member 42. In another preferred embodiment the connecting member 42 extends perpendicular to the cutting mechanism and through the body 32 to the situating mechanism 44 (FIG. 2).

If the cutting mechanism is not the flexible blade 31 or if alternative surgical instruments other than cutting mechanisms 31 are received within internal chamber 33, a connecting member 42 may be used, an alternative connecting member may be used, or no connecting mechanism may be used. For example, a laser cutter may use an optical fiber enclosed in a rigid tubular housing as a connecting member 42. As another example, a cautery may use an insulated shaft covering electrically conductive wires as a connecting member 42. In yet another example, a rotary cutter may require a connecting mechanism capable of transferring rotational mechanical energy, such as driveshaft enclosed in a housing.

The Actuating Means. The term "actuating mechanism 54" refers to any device that may be used to cause an instrument to perform its designated function. In one preferred embodiment, an actuating mechanism 54 may be used to rotate the percutaneous cellulite removal needle 30 to cut fibrous bridges 28. In alternative embodiments, actuating mechanisms might include mechanisms for starting and/or controlling surgical instruments such as endoscopes or aspirators.

Figure 3:
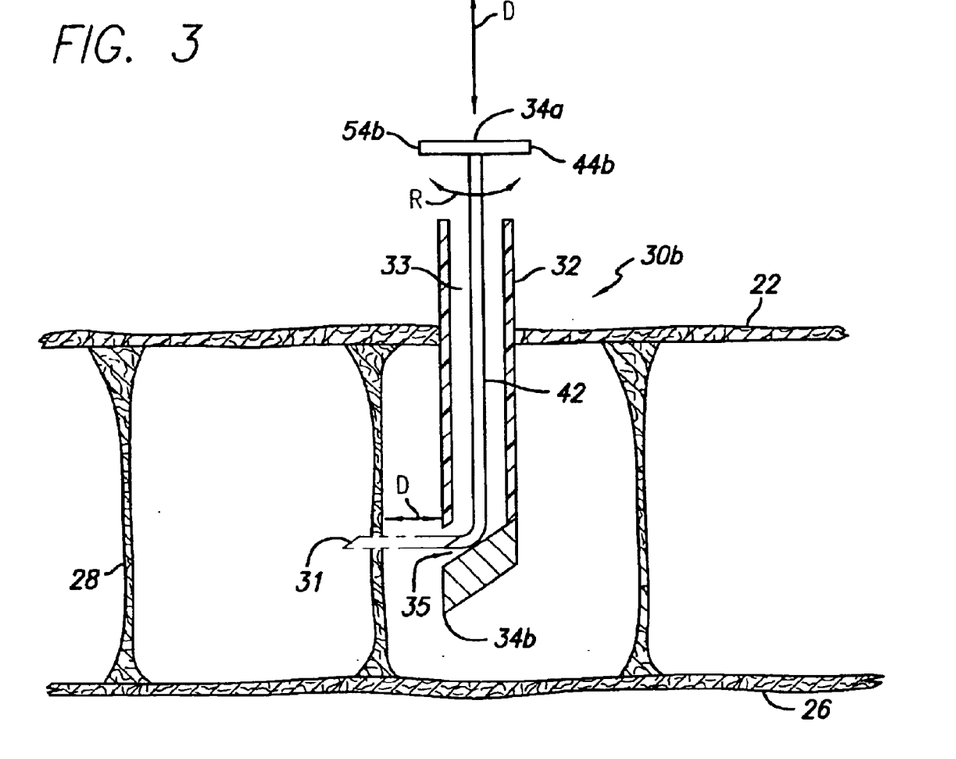
FIG. 3 is a side cross-sectional view of a second exemplary embodiment of the percutaneous cellulite removal needle of the present invention.
Figure 4:
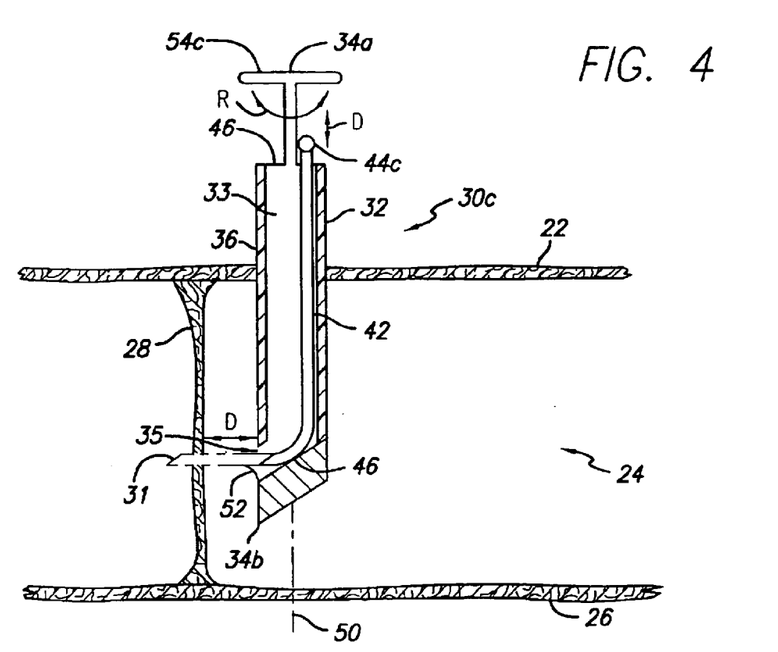
FIG. 4 is a side cross-sectional view of a third exemplary embodiment of the percutaneous cellulite removal needle of the present invention.

Exemplary actuating mechanisms 54 (the reference numeral 5 (as shown in FIG. 8) is a general reference to any type of actuating mechanism including, but not limited to exemplary situating mechanisms 54a–54h (shown in phantom in FIG. 1)) may include the housing 54a (FIG. 2) that can be rotated between a user's fingers, a movable handle 54b (FIG. 3), or a fixed handle 54c (FIG. 4). Alternative actuating mechanisms 54 may include levers 54d, dials 54e, ratchets 54f, buttons 54g, or any other similar device or apparatus 54h that causes the cutting mechanism 31 to sever fibrous bridges 28. These actuating mechanisms 54 are meant to be exemplary and are not meant to limit the scope of the invention.

In the embodiment of FIG. 2, the actuating mechanism 54a is the exterior housing 54a that may be rotated by a user so that the cutting mechanism is rotated about the longitudinal axis. In this embodiment the percutaneous cellulite removal needle 30 can also be actuated using the housing 54a by pushing in and pulling out the entire needle, moving the needle back and forth, or making saw-like motions.

FIGS. 3, 4, and 8 show another preferred embodiment where the T-handle actuating mechanism 54b, 54c rotates the percutaneous cellulite removal needle 30 and/or cutting mechanism 31 about the longitudinal axis. In this embodiment, the rotating motion is indicated by the directional action arrows "R." In the shown embodiment, as the percutaneous cellulite removal needle 30 is rotated, the sharp side-edge (shown as 31a in FIG. 8) of flexible blade 31 severs fibrous bridges 28.

In another preferred embodiment the percutaneous cellulite removal needle 30 is actuated when a blade 31 with a sharp tip moves forward (e.g. protruding out of the needle 30) and backward to cut fibrous bridges 28. This actuating movement is shown in the figures as motion D. For example, when an actuating mechanism 54 is pushed down, the sharp tip moves forward to cut fibrous bridges 28 in front of it and, when the actuating mechanism 54 is pulled up, sharp tip is pulled in and reset for future cutting. In yet another preferred embodiment a serrated blade may be used that may also cut on backward movement.

Additional or Optional Features. FIG. 5 shows several exemplary additional or optional features that may be incorporated into any of the embodiments of the present invention. For example, FIG. 5 shows exemplary additional or optional substantially solid needle body 32'. Another exemplary additional or optional feature is a blunt distal end 34b'. Yet another exemplary additional or optional feature is a cover 52 that covers the lateral aperture 35. This cover could be the cover of FIG. 4 in the closed position. The cover shown 52 is self-sealing.

Figure 6:
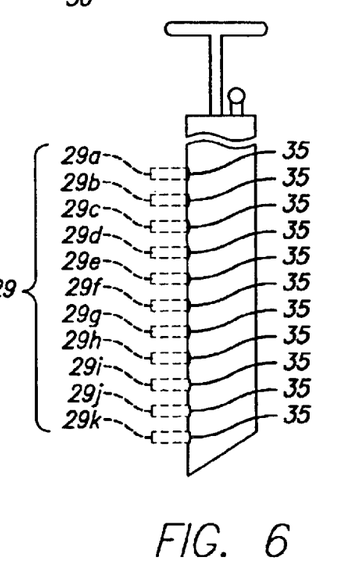
FIG. 6 is a side view of an exemplary embodiment of the percutaneous cellulite removal needle of the present invention showing a cutting mechanism in a cutting position, an endoscope in an operative position, and an aspiration in an operative position.
Figure 7:
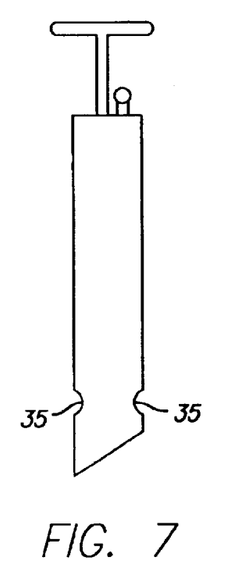
FIG. 7 is a side view of an exemplary embodiment of the percutaneous cellulite removal needle of the present invention showing two lateral apertures formed in the outer peripheral surface on opposite sides of the percutaneous cellulite removal needle.

FIGS. 6 and 7 show exemplary or optional additional lateral apertures (which may be sealed with optional covers (not shown)) through which other surgical instruments 29 may be used alone or in combination with the cutting mechanism 31. In addition to surgical instruments 29 such as cutting mechanisms 31. (e.g. a flexible blade (shown as 29a in FIG. 6), cautery (shown as 29b in FIG. 6), a harmonic scalpel (shown as 29c in FIG. 6), an ultrasonic cutting instrument (shown as 29d in FIG. 6), a rotary cutter (shown as 29e in FIG. 6), a laser cutter (shown as 29f in FIG. 6), an oscillating saw (shown as 29g in FIG. 6), and/or a saw blade (shown as 29h in FIG. 6) other surgical instruments 29 may include, for example, an endoscope (shown as 29i in FIG. 6), an aspirator (shown as 29j in FIG. 6), and/or an irrigation mechanism (shown as 29k in FIG. 6). An embodiment including multiple apertures may be used to view a surgical site and to simultaneously perform both liposuction and sever fibrous bridges 28 or septae. In one preferred embodiment, a mechanism for visualizing a surgical site, such as an endoscope or other visualizing instrument, is used with the percutaneous cellulite removal needle 30. In another preferred embodiment, a mechanism for aspirating a surgical site is used with percutaneous cellulite removal needle 30. The mechanism for aspirating may be any surgical aspirator. In still another preferred embodiment, an irrigation mechanism is used with percutaneous cellulite removal needle 30. The irrigation mechanism would be used for introducing irrigation or fluid to increase tissue tumescense and accentuate the appearance of cellulite by tightening fibrous bridges or septae. In these multiple lateral aperture embodiments, it is contemplated that the other surgical instruments 29 may be used alone or in combination with the cutting mechanism 31. For example, using the embodiment of FIG. 6 an endoscope, an aspirator, and a cutting mechanism 31 may be used simultaneously.

It should be noted that alternative surgical instruments 29 (e.g. endoscopes (shown as 29j in FIG. 6), aspirators (shown as 29i in FIG. 6), and/or irrigation mechanisms (shown as 29k in FIG. 6)) can be used alone in place of the cutting mechanism 31 in a single lateral aperture embodiment. Further, the alternative surgical instruments 29 may be used in various combinations in a multiple lateral aperture embodiment.

Another additional or optional feature, as shown in FIG. 2, is a depth indicator 60. As shown, the depth indicator 60 may be markings near the distal end 35b that clearly set forth measurements. The depth indicator 60 may be, for example, a numerical or a color coded indicator.

Yet another additional or optional feature (not shown) is a needle sheath that serves to protect tissue from the cutting mechanism 31 until the cutting mechanism 31 is completely extended and in the correct position for cutting.

It should be noted that the present invention may be used for the exemplary stated purposes. Further, the present invention may be used for adhesions. Still further, the present invention may be used as an endoscopic or arthroscopic cutting device. Although the present invention may be used manually, in alternative preferred embodiments it may be manipulated by machines.

It should be noted that other embodiments not shown or discussed could be used to implement the present invention. For example, a "ball-point pen" embodiment could be developed where pushing a button causes the blade to retract or protrude and it is held in position by a spring and notch mechanism. Other embodiments could use blades that telescope or unwind.

First Embodiment Example. Referring to in FIG. 2, a first exemplary preferred embodiment of the present invention of the percutaneous cellulite removal needle 30a includes a thick flexible and retractable blade 31. An extrusion mechanism is the situating mechanism 44a that controls the transition of the flexible blade 31 between a retracted position in which the flexible blade 31 is within the internal chamber 33 and a cutting position (in phantom) in which the flexible blade 31 extends through the lateral aperture 35 to the side of the percutaneous cellulite removal needle 30a. The plastic housing 32 serves as the actuating mechanism 54a as the surgeon rotates the housing 32 between his fingers so that the flexible blade 31 rotates to cut fibrous bridges 28.

Second Embodiment Example. Referring to FIG. 3, a second exemplary preferred embodiment of the present invention of the percutaneous cellulite removal needle 30b includes a flexible and retractable blade 31 that is connected directly or indirectly to a handle 44b, 54b that serves both as the situating mechanism 44b and the actuating mechanism 54b. In this embodiment the lateral aperture 35 is an elongated slot perpendicular to the longitudinal axis of the needle 30. By pushing the handle up and down it acts as the situating mechanism 44b that controls the transition of the flexible blade 31 between a retracted position and the cutting position (in phantom). In this embodiment the body 32 is held in place and, by rotating the handle 54b it acts as the actuating mechanism 54b and moves the blade 31 within the elongated slot lateral aperture 35. Alternatively, the body 32 may be rotated to act as the actuating mechanism 54b.

Third Embodiment Example. Referring to FIG. 4, a third exemplary preferred embodiment of the present invention of the percutaneous cellulite removal needle 30c includes a flexible and retractable blade 31 within a chamber. At the closed proximal end 34a of this embodiment is a T-handle 54c that serves as the actuating mechanism. A separate situating mechanism such as a dial 44c is preferably connected directly or indirectly to the flexible blade 31 and may be moved (perhaps by rotating) between two positions to control the transition of the flexible blade 31 between a retracted position and the cutting position. Rotating the T-handle 54c while the flexible blade 31 is in the cutting position causes the blade 31 to rotate and sever fibrous bridges 28. The embodiment shown in this figure also includes an optional cover 52 that covers the lateral aperture 35. In one preferred embodiment, cover 52 helps hold flexible blade 31 in a substantially perpendicular cutting position by providing a perpendicular support surface.

Dimensions. In one preferred embodiment, the percutaneous cellulite removal needle 30 is a large bore (1.5–2.0 mm) percutaneous cellulite removal needle, such as a 12 or 14 gauge needle. In an alternative preferred embodiment, the percutaneous cellulite removal needle 30 would have a length of 15 cm and an outer diameter of 6 mm. The internal chamber 33 of the percutaneous cellulite removal needle 30 is preferably of sufficient size (diameter up to 4 mm) to accommodate one or more instruments. Similarly, the lateral opening in the peripheral surface of the percutaneous cellulite removal needle 30 is preferably of sufficient size (diameter up to 2 mm) to form a passageway for at least one of the instruments. These dimensions are exemplary and other dimensions are contemplated depending on the surgical site, the dimensions of the cutting mechanism 31 and/or other instrument(s), the size of the patient (for example, there may be small, medium, and large embodiments), and other size related factors.

METHODS

Figure 9:
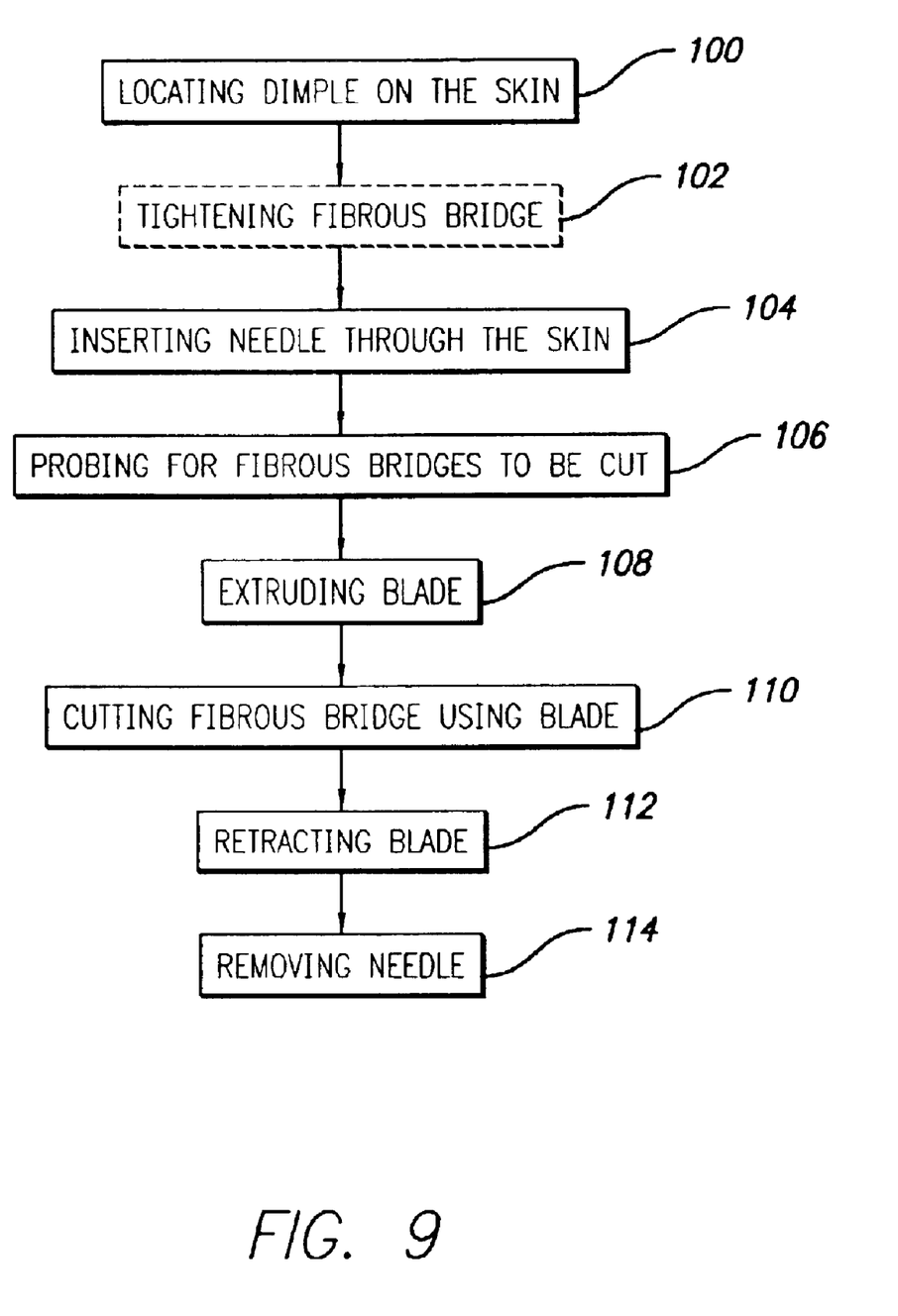
FIG. 9 is a flow chart showing an exemplary method of the present invention.
Figure 10:
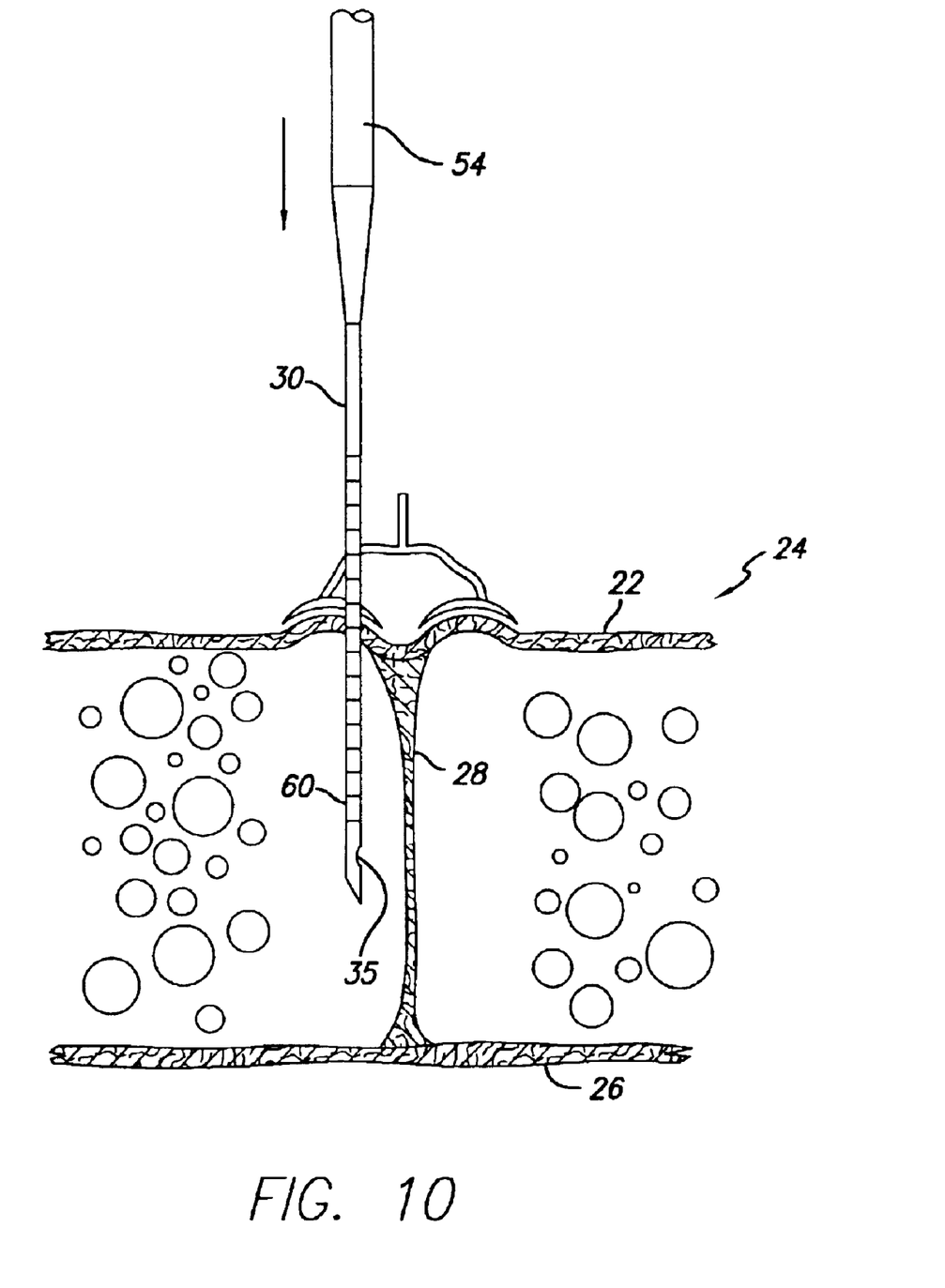
FIGS. 10–12 illustrate exemplary steps of the method of FIG. 9.
Figure 11:
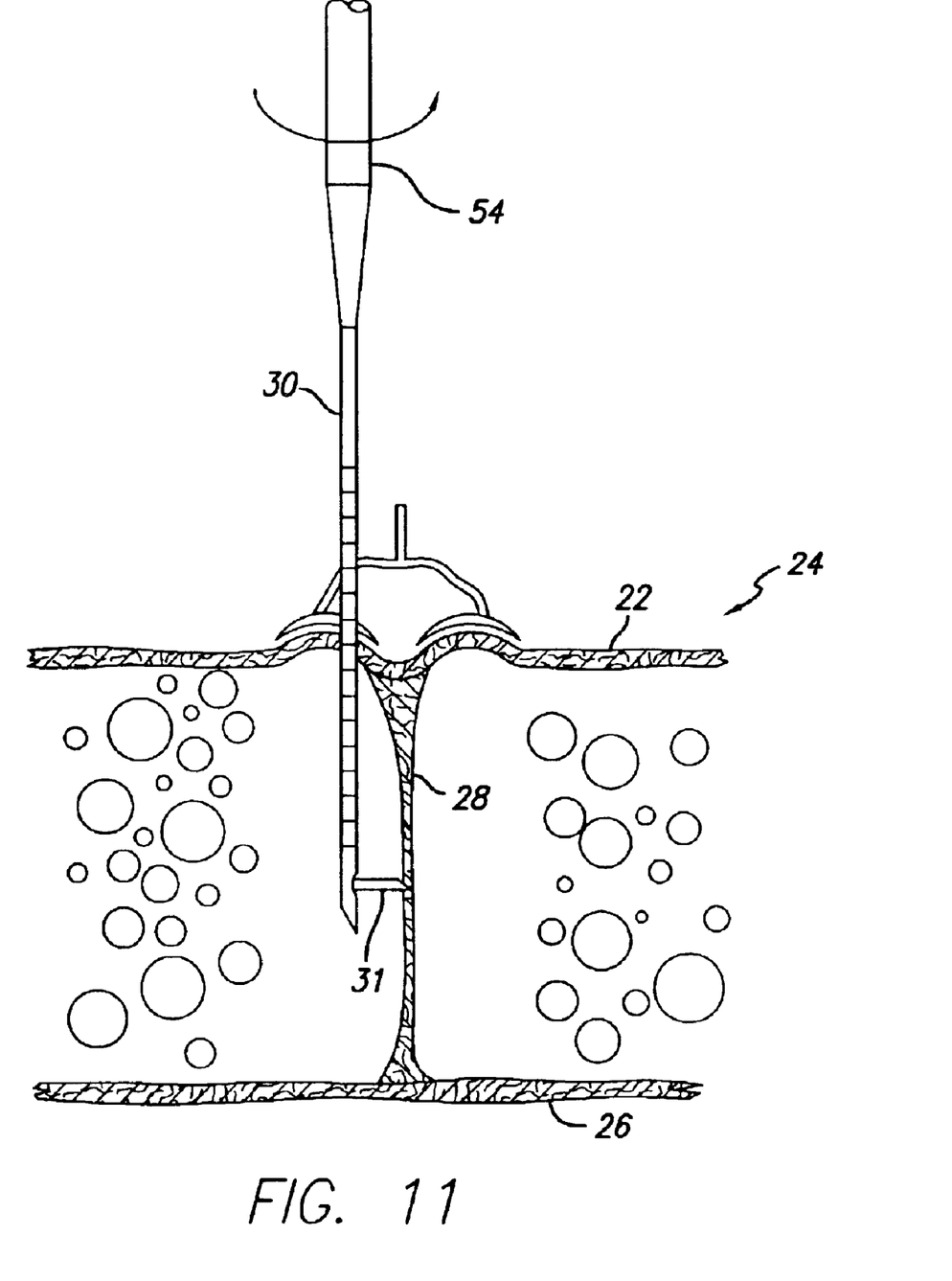
Figure 12:
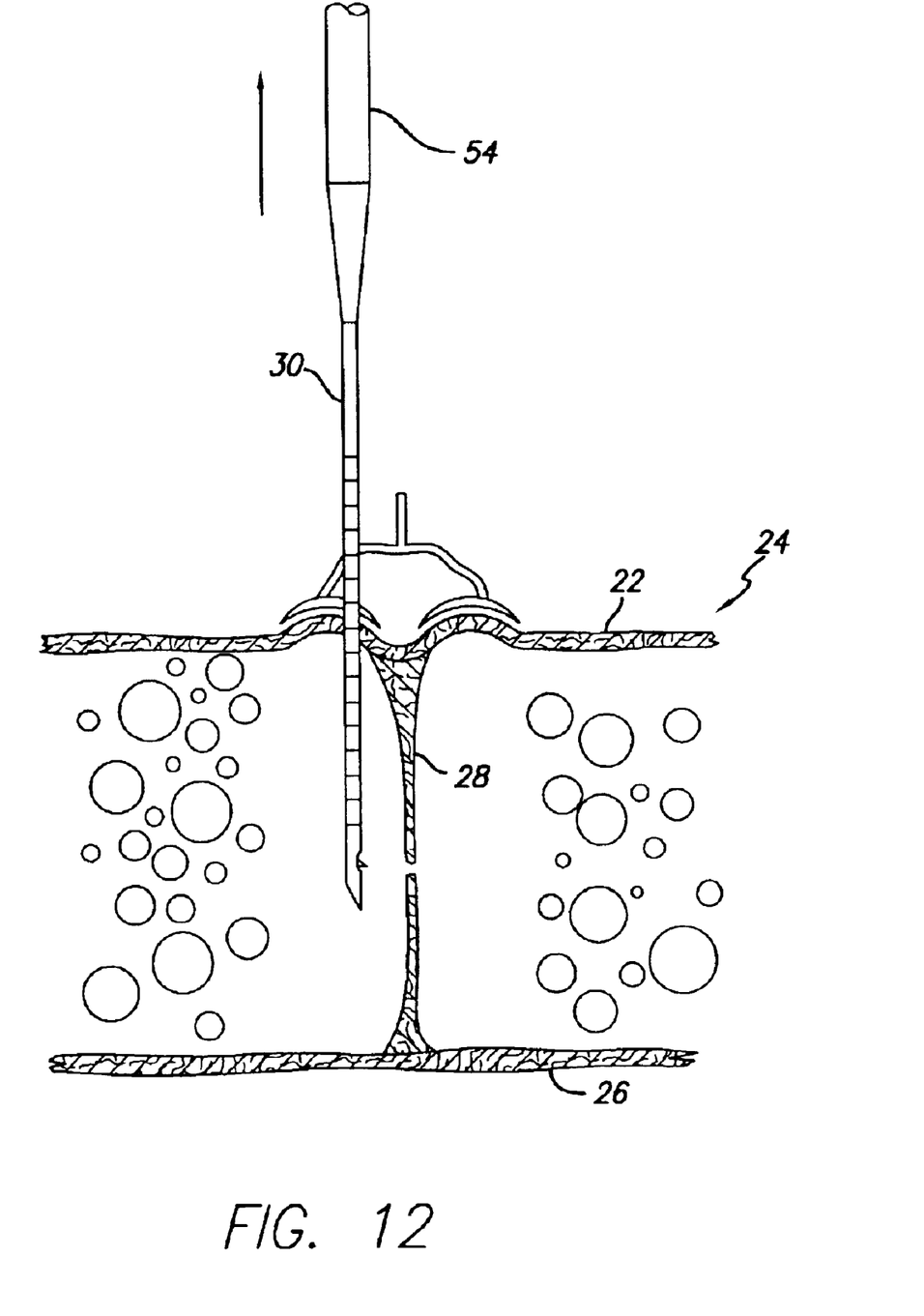

The present invention is also directed to methods for cutting the fibrous bridges 28 that connect the dermis 22 to muscle/fascia 26 in a minimally invasive manner. For purposes of illustrating one preferred method of the present invention, reference is made to the preferred embodiment of the percutaneous cellulite removal needle 30 shown in FIG. 2. It will be assumed that standard medical practices (e.g. sterilization and anesthesia) will be observed and, therefore, are not discussed as part of this exemplary method. FIG. 9 shows the basic steps of the exemplary method and FIGS. 10–12 show graphical representations of some of the steps.

The first step is preferably to locate at least one dimple on the skin 100. This step could be avoided if, for example, the remaining steps are practiced in a systematic manner (e.g. by insertion of the percutaneous cellulite removal needle 30 at regular intervals). Alternatively, this step could be avoided or reduced by a series of random insertions where to provide a quick start to the procedure and, after a majority of fibrous bridges 28 have been cut, the step of locating the dimples could be practiced.

Next, the fibrous bridge 28 may be tightened 102. FIG. 10 illustrates a method for performing this step using a suction device to gently lift the skin around the fibrous bridge 28. Using suction the user can lift the area of treatment, accentuating tension on the fibrous band 28. Alternative methods could be using adhesive in place of the suction or simply pinching the skin around the fibrous bridge 28. It should be noted that this step is optional, can be performed before or after insertion, and can be accomplished using alternative methods. Another example of an alternative method to ease visualization could be to inject fluid (either using the percutaneous cellulite removal needle 30 or via a separate injection needle) to cause tension on the fibrous band. A small wheal of local anesthetic can optionally be administered.

The percutaneous cellulite removal needle 30 is then inserted through the skin 104. Specifically, the distal end 34b of the percutaneous cellulite removal needle 30 is inserted through the skin with the cutting mechanism 31 in a retracted position. For example, with the cutting mechanism 31 in its retracted position, the handle 54 may be used to push the percutaneous cellulite removal needle 30 through the skin 24 until the lateral aperture 35 reaches the desired depth. It should be noted that the depth indicator 60 could be used to verify the depth of the lateral aperture 35. The percutaneous cellulite removal needle 30 may then be used to probe for one or more fibrous bridge 28 to be cut 106.

In one alternative embodiment, the percutaneous cellulite removal needle 30 has a blunt distal end 34b and, therefore, a separate instrument may be used to make an insertion in the skin 24. The percutaneous cellulite removal needle 30 is then inserted into the insertion to probe for and/or cut the fibrous bridge 28. In another alternative embodiment, a separate instrument may be used to probe for fibrous bridges 28 to be cut.

Once a fibrous bridge 28 is found, the cutting mechanism 31 is extruded 108 using the situating mechanism 44. As shown in FIG. 11, in one preferred embodiment of the method, the extruding may be through the side of the percutaneous cellulite removal needle 30. In one preferred embodiment, by activating the situating mechanism 44, the connecting member 42 forces the cutting mechanism 31 from its retracted position within the internal chamber 33, through lateral aperture 35, and into its cutting position.

Then, using the actuating mechanism 54, the cutting mechanism 31 is actuated so as to cut the fibrous bridge 110.

In one preferred embodiment the cutting is accomplished by rotating the percutaneous cellulite removal needle 30. Using the percutaneous cellulite removal needle 30 of FIG. 2, the activating mechanism 54a may be used to turn the percutaneous cellulite removal needle 30 about its longitudinal axis. As the percutaneous cellulite removal needle 30 is turned, the cutting mechanism 31 severs one or more fibrous bridge 28 located within a radius of percutaneous cellulite removal needle 30 defined by the length of the cutting mechanism 31.

As shown in FIG. 12, the cutting mechanism 31 may then be retracted 112 and the percutaneous cellulite removal needle 30 may either be used to further probe for more fibrous bridges 28 or removed 114.

The steps set forth above are preferably repeated. The procedure may be done in a staged fashion. For example, after the percutaneous cellulite removal needle 30 has been rotated 360°, the procedure may be repeated at another location at the surgical site until all fibrous bands at the surgical site have been severed.

While a preferred method of the present invention has been described with reference to one preferred embodiment, it will be appreciated that this method may be appropriately modified to accommodate other embodiments of the present invention. For example, the step of turning or rotating the percutaneous cellulite removal needle 30 to sever fibrous bridges 28 may be modified so that the cutting mechanism 31 is moved in the direction of action arrow D to sever fibrous bridges 28 or as the cutting mechanism may require. Further, although the disclosure focused on fibrous bridges 28, the same principles can be applied to fibrous septae in subcutaneous fat.

The terms and expressions that have been employed in the foregoing specification are used as terms of description and not of limitation, and are not intended to exclude equivalents of the features shown and described or portions of them. The scope of the invention is defined and limited only by the claims that follow.

What is claimed is:

1. A method for cutting fibrous bridges that connect skin to muscle/fascia or the fibrous septae in subcutaneous fat in a minimally invasive manner, using a percutaneous cellulite removal needle having a body with an internal chamber and a cutting mechanism, said cutting mechanism substantially positioned within said first internal chamber in a retracted position and at least partially protruding from said body in a cutting position, said method comprising the steps of:
   (a) inserting said percutaneous cellulite removal needle through said skin with said cutting mechanism in said retracted position;
   (b) extruding said cutting mechanism so that said cutting mechanism is in said cutting position;
   (c) actuating said cutting mechanism;
   (d) cutting at least one said fibrous bridge;
   (e) repeating step (d) for fibrous bridges reachable by said cutting mechanism;
   (f) retracting said cutting mechanism; and
   (g) removing said percutaneous cellulite removal needle through said skin with said cutting mechanism in said retracted position.

2. The method of claim 1 wherein steps (a)–(g) may be repeated in different locations.

3. The method of claim 1 further comprising the step of locating a dimple on said skin.

4. The method of claim 1 further comprising the step of tightening said fibrous bridge or septae.

5. The method of claim 4 wherein said step of tightening said fibrous bridge or septae further comprises the step of lifting the skin around said fibrous bridge.

6. The method of claim 4 wherein said step of tightening said fibrous bridge or septae further comprises the step of lifting the skin around said fibrous bridge using suction.

7. The method of claim 4 wherein said step of tightening said fibrous bridge or septae further comprises the step of injecting fluid around said fibrous bridge.

8. The method of claim 1 further comprising the step of probing for fibrous bridges or septae to be cut.

9. The method of claim 1, wherein said step of extruding said cutting mechanism further comprises the step of extruding said cutting mechanism through a laterally disposed aperture defined in said body.

10. The method of claim 1, wherein said step of extruding said cutting mechanism further comprises the step of extruding said cutting mechanism using a situating mechanism.

11. The method of claim 1, wherein said step of actuating said cutting mechanism further comprises the step of rotating said percutaneous cellulite removal needle.

12. The method of claim 1, wherein said step of actuating said cutting mechanism further comprises the step of rotating said cutting mechanism.

13. A percutaneous cellulite removal needle for cutting fibrous bridges that connect skin to muscle/fascia in a minimally invasive manner, said percutaneous cellulite removal needle comprising:
   (a) a body comprising:
      (i) a proximal end;
      (ii) an outer peripheral surface;
      (iii) a first internal chamber defined within said outer peripheral surface; and
      (iv) a distal end substantially opposite said proximal end;
   (b) a first laterally disposed aperture defined in said outer peripheral surface between said proximal end and said distal end, said first internal chamber ending at said first laterally disposed aperture;
   (c) a cover at least partially covering said first laterally disposed aperture, wherein said cover is self-sealing;
   (d) a cutting mechanism, said cutting mechanism substantially positioned within said first internal chamber in a retracted position and at least partially protrudes through said laterally disposed aperture in a cutting position; and
   (e) means for situating said cutting mechanism between said retracted position and said cutting position.

14. The percutaneous cellulite removal needle of claim 13, wherein said distal end is adapted to penetrate tissue.

15. The percutaneous cellulite removal needle of claim 13, wherein said distal end is blunt.

16. The percutaneous cellulite removal needle of claim 13, wherein said means for situating is selected from a group consisting of:
   (a) an extrusion mechanism;
   (b) a button;
   (c) a lever;
   (d) a handle;
   (e) a dial; and
   (f) a ratchet.

17. The percutaneous cellulite removal needle of claim 13, wherein said cutting mechanism is selected from a group consisting of:
   (a) a flexible blade;
   (b) a cautery;

(c) a harmonic scalpel;
(d) an ultrasonic cutting instrument;
(e) a rotary cutter;
(f) a laser cutter; and
(g) an oscillating saw.

18. The percutaneous cellulite removal needle of claim 13 further comprising an actuating mechanism for actuating said cutting mechanism.

19. The percutaneous cellulite removal needle of claim 18, wherein said actuating mechanism causes said cutting mechanism to cut fibrous bridges.

20. The percutaneous cellulite removal needle of claim 18, wherein said actuating mechanism is selected from a group consisting of:
    (a) said body;
    (b) a movable handle;
    (c) a fixed handle; and
    (d) means for rotating said cutting mechanism.

21. The percutaneous cellulite removal needle of claim 13 further comprising a depth indicator.

22. The percutaneous cellulite removal needle of claim 13 further comprising:
    (a) a second internal chamber defined within said outer peripheral surface;
    (b) a second laterally disposed aperture defined in said outer peripheral surface between said proximal end and said distal end, said second internal chamber ending at said second laterally disposed aperture;
    (c) a surgical instrument, said surgical instrument substantially positioned within said second internal chamber in a retracted position and at least partially protrudes through said laterally disposed aperture in an actuated position; and
    (d) means for situating said surgical instrument between said retracted position and said actuated position.

23. The percutaneous cellulite removal needle of claim 13, wherein said cutting mechanism is a flexible cutting mechanism.

24. The percutaneous cellulite removal needle of claim 13, further comprising a guide surface for guiding said cutting mechanism from its retracted position to its cutting position.

25. A percutaneous cellulite removal needle for cutting fibrous bridges that connect skin to muscle/fascia in a minimally invasive manner, said percutaneous cellulite removal needle comprising:
    (a) a body comprising:
        (i) a proximal end;
        (ii) an outer peripheral surface;
        (iii) a first internal chamber defined within said outer peripheral surface; and
        (iv) a distal end substantially opposite said proximal end;
    (b) a first laterally disposed aperture defined in said outer peripheral surface between said proximal end and said distal end, said first internal chamber ending at said first laterally disposed aperture;
    (c) a cutting mechanism, said cutting mechanism substantially positioned within said first internal chamber in a retracted position and at least partially protrudes through said laterally disposed aperture in a cutting position;
    (d) means for situating said cutting mechanism between said retracted position and said cutting position; and
    (e) a cover at least partially covering said first laterally disposed aperture, wherein said cover has a closed position and an open position, said cover being in said open position and holding said cutting mechanism in a substantially perpendicular position to said body when said cutting mechanism is in said cutting position.

26. The percutaneous cellulite removal needle of claim 25, wherein said distal end is adapted to penetrate tissue.

27. The percutaneous cellulite removal needle of claim 25, wherein said distal end is blunt.

28. The percutaneous cellulite removal needle of claim 25, wherein said means for situating is selected from a group consisting of:
    (a) an extrusion mechanism;
    (b) a button;
    (c) a lever;
    (d) a handle;
    (e) a dial; and
    (f) a ratchet.

29. The percutaneous cellulite removal needle of claim 25, wherein said cutting mechanism is selected from a group consisting of:
    (a) a flexible blade;
    (b) a cautery;
    (c) a harmonic scalpel;
    (d) an ultrasonic cutting instrument;
    (e) a rotary cutter;
    (f) a laser cutter; and
    (g) an oscillating saw.

30. The percutaneous cellulite removal needle of claim 25, further comprising an actuating mechanism for actuating said cutting mechanism.

31. The percutaneous cellulite removal needle of claim 30, wherein said actuating mechanism causes said cutting mechanism to cut fibrous bridges.

32. The percutaneous cellulite removal needle of claim 30, wherein said actuating mechanism is selected from a group consisting of:
    (a) said body;
    (b) a movable handle;
    (c) a fixed handle; and
    (d) means for rotating said cutting mechanism.

33. The percutaneous cellulite removal needle of claim 25, further comprising a depth indicator.

34. The percutaneous cellulite removal needle of claim 25, further comprising:
    (a) a second internal chamber defined within said outer peripheral surface;
    (b) a second laterally disposed aperture defined in said outer peripheral surface between said proximal end and said distal end, said second internal chamber ending at said second laterally disposed aperture;
    (c) a surgical instrument, said surgical instrument substantially positioned within said second internal chamber in a retracted position and at least partially protrudes through said laterally disposed aperture in an actuated position; and
    (d) means for situating said surgical instrument between said retracted position and said actuated position.

35. The percutaneous cellulite removal needle of claim 25, wherein said cutting mechanism is a flexible cutting mechanism.

36. The percutaneous cellulite removal needle of claim 25, further comprising a guide surface for guiding said cutting mechanism from its retracted position to its cutting position.

* * * * *

UNITED STATES PATENT AND TRADEMARK OFFICE
CERTIFICATE OF CORRECTION

PATENT NO. : 6,916,328 B2
DATED : July 12, 2005
INVENTOR(S) : Darrell C. Brett

It is certified that error appears in the above-identified patent and that said Letters Patent is hereby corrected as shown below:

Column 4,
Line 15, "30i a(FIG. 2)," should read -- 30a (FIG. 2), --; and
Line 64, "passage way" should read -- passageway --.

Column 5,
Line 46, "20" should read -- 30 --.

Column 6,
Line 42, "maybe" should read -- may be --.

Column 8,
Line 8, "mechanism 31." should read -- mechanisms 31, --;
Line 14, "FIG. 6)" should read -- FIG. 6)), --;
Line 39, "29j" should read -- 29i --; and
Line 40, "29i" should read -- 29j --.

Column 9,
Line 3, "to in" should read -- to --.

Column 14,
Line 42, "25," should read -- 25 --.

Signed and Sealed this

Fourteenth Day of March, 2006

JON W. DUDAS
*Director of the United States Patent and Trademark Office*